United States Patent

Yano et al.

[11] 4,443,459
[45] Apr. 17, 1984

[54] α-TOCOPHERYL ESTER OF 5-SUBSTITUTED PICOLINIC ACID AND HYPOTENSIVE COMPOSITION CONTAINING IT

[75] Inventors: Mitsuo Yano, Yokohama; Junji Yoshizawa, Machida; Kiyofumi Ishikawa, Chofu; Nobuo Harada, Okazaki; Ikuo Matsumoto, Tokyo, all of Japan

[73] Assignee: Banyu Pharmaceutical Co., Ltd., Tokyo, Japan

[21] Appl. No.: 379,060

[22] Filed: May 19, 1982

[30] Foreign Application Priority Data

May 26, 1981 [JP] Japan .................................. 56-78702
Apr. 13, 1982 [JP] Japan .................................. 57-60359

[51] Int. Cl.³ .................... C07D 405/12; A61K 31/44
[52] U.S. Cl. ..................................... 424/266; 546/269
[58] Field of Search ......................... 546/269; 424/266

[56] References Cited

U.S. PATENT DOCUMENTS 4,198,416 4/1980 Koeda et al. ...................... 546/269

Primary Examiner—John M. Ford
Assistant Examiner—Bernard Dentz
Attorney, Agent, or Firm—Sherman & Shalloway

[57] ABSTRACT

An α-tocopheryl 5-substituted picolinate of the formula

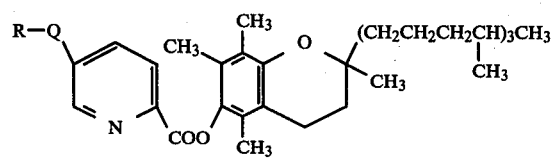

wherein R represents an alkyl group which may have a substituent, a lower alkenyl group, a phenyl(lower alkyl) group, or a phenyl group which may have a substituent, and Q represents a methylene group or an oxygen or sulfur atom, or a pharmaceutically acceptable acid addition salt thereof. This compound can be produced by reacting a substituted picolinic acid of the formula

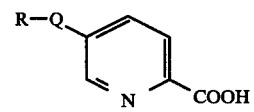

wherein R and Q are as defined above, or its reactive derivative with α-tocopherol of the formula

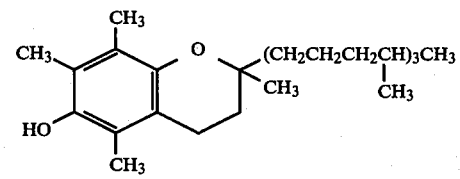

and as required, contacting the resulting compound with a pharmaceuticlly acceptable acid. A pharmaceutical composition comprising said compound as an active ingredient is useful for the treatment of hypertension.

26 Claims, No Drawings

α-TOCOPHERYL ESTER OF 5-SUBSTITUTED PICOLINIC ACID AND HYPOTENSIVE COMPOSITION CONTAINING IT

This invention relates to a novel 5-substituted picolinic acid ester, a process for its production and a pharmaceutical composition comprising said ester as an active ingredient which is useful for the treatment of hypertension.

More specifically, this invention relates to an α-tocopheryl 5-substituted picolinate of the general formula

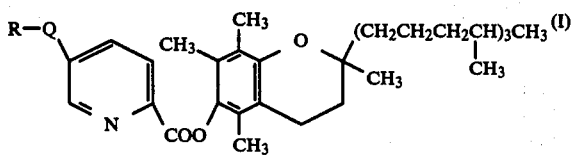

wherein R represents an alkyl group which may have a substituent, a lower alkenyl group, a phenyl(lower alkyl) group, or a phenyl group which may have a substituent, and Q represents a methylene group or an oxygen or sulfur atom, or its pharmaceutically acceptable acid addition salt; and also to a process for producing the compound of formula (I) and to its use.

The novel 5-substituted picolinic acid esters of this invention have an excellent, long-lasting hypotensive action suitable for long-term administration for the prevention and treatment of hypertension without any appreciable side-effects, and their toxicity is extremely low.

Among known 5-substituted picolinic acids typified by 5-butylpicolinic acid are included many compounds which have dopamine β-hydroxylase inhibiting activity and hypotensive activity, as shown, for example, in Japanese Laid-Open Patent Publications Nos. 574/1973, 39481/1973, 7290/1974, 20183/1974, 76873/1974, 86468/1976, 86469/1976, 86470/1976, 86471/1976, 83668/1977, and 125681/1979. It is known however that these previously known 5-substituted picolinic acids are acidic compounds, and in oral administration, may induce gastric troubles. Since they have relatively strong toxicity, their use is limited.

We have now found that α-tocopheryl 5-substituted picolinates not described in the prior literature can be produced by esterifying 5-substituted picolinic acids with α-tocopherol, and that these novel compounds have a long-lasting hypotensive activity without the toxicity and side-effects of the known 5-substituted picolinic acids. It has also been found that the novel compounds can be expected to be used for the prevention and treatment of arteriosclerosis and thrombosis because they have an antiarteriosclerotic or antithrombotic activity, as reflected in the inhibition of formation of accumulation of lipid peroxides, the protection of vascular tissues, the improvement in lipid metabolism, or the prevention of platelet aggregation.

It is well known that arteriosclerosis or thrombosis occurs easily on the injured vascular beds, and statistically, hypertension is cited as the first risk factor. It is said therefore that hypertensive persons must make an effort to maintain their blood pressure at a normal level by using hypotensors in order to prevent the onset of serious circulatory troubles as arteriosclerosis or thrombosis. Since it is usual to administer hypotensors for a long period of time to persons with essential and other types of hypertension, the hypotensors are required to have minimum toxicity and side-effects. It is quite desirable that the hypotensors have an action of not only lowering the blood pressure, but also of improving circulation, inhibiting the formation or accumulation of lipid peroxides, preventing ageing of vascular tissues, stabilizing cell membranes, inhibiting the tendency of thrombus formation, or exciting the function of microcirculation.

Investigations of the present inventors have shown that the novel compounds of formula (I) can exhibit the aforesaid desirable properties.

It is an object of this invention to provide novel compounds represented by formula (I).

Another object of this invention is to provide a process for producing the compounds of formula (I), and a pharmaceutical composition useful for the treatment of hypertension which comprises the compound of formula (I).

The above and other objects of this invention will become more apparent from the following description.

In the general formula (I) above, R represents an alkyl group which may be have a substituent, a lower alkenyl group, a phenyl(lower alkyl) group, or a phenyl group which may have a substituent.

The alkyl group may be a linear or branched $C_1$–$C_8$ alkyl group. Specific examples of the alkyl group are methyl, ethyl, propyl, isopropyl, butyl, sec-butyl, pentyl, isopentyl, and octyl groups. The alkyl group may have a substituent or substituents selected from the class consisting of halogen atoms such as chlorine or bromine, acetoxy groups, hydroxyl groups and $C_1$–$C_4$ alkyl ether groups. The alkyl groups may be mono- or di-substituted by these substituents. Examples of the substituted alkyl groups are 3-bromopropyl, 3-chloropropyl, 3-acetoxypropyl, 2-chloropropyl, 3,4-dibromopropyl, 3,4-dichloropropyl, and 4-chlorobutyl groups.

The lower alkenyl group for R may be a $C_2$–$C_5$ alkenyl group, such as a vinyl or allyl group. Examples of the phenyl(lower alkyl) for R are phenyl ($C_1$–$C_2$ alkyl) groups, such as a benzyl or phenethyl group.

Examples of the phenyl group which may have a substituent are mono- or di-substituted phenyl groups having a substituent or substituents selected from the class consisting of nitro groups and halogen atoms such as chlorine or bromine. When it has two or more substituents, they may be identical or different.

The compound of formula (I) can be produced, for example, by reacting a 5-substituted picolinic acid of the following formula

wherein R and Q are as defined above, or its reactive derivative, with α-tocopherol of the following formula

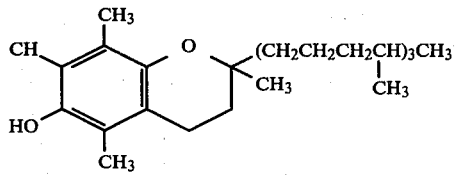
(III)

The reactive derivative may be an ester-forming derivative, for example, acid halides, such as bromide or chloride, of the 5-substituted picolinic acid of formula (II), and an acid anhydride of the 5-substituted picolinic acid of formula (II).

The reaction can also be carried out in the presence of a dehydrocondensing agent. In particular, when the 5-substituted picolinic acid is used, the reaction is carried out preferably in the presence of a dehydrocondensing agent. Examples of the dehydrocondensing agent are dicyclohexylcarbodiimide and phosphorus oxychloride.

When the dehydrocondensing agent is used, the reaction is carried out in an aprotic solvent such as hexane, methylene chloride, chloroform, toluene, dimethyl formamide, tetrahydrofuran and pyridine. The mole ratio of the 5-substituted picolinic acid/α-tocopherol/- the dehydrating agent is usually in the range of 1.0/5–5.0/0.5–10.0, preferably 1.0/0.8–1.5/1.0–2.0. When phosphorus oxychloride is used as the dehydrocondensing agent, at least 1 mole, per mole of the dehydrocondensing agent, of a tertiary amine such as triethylamine or pyridine is used. The reaction is carried out usually at −20° C. to the boiling point of the solvent, preferably at 0° C. to room temperature. When the 5-substituted picolinic acid halide is used, the 5-substituted picolinic acid and a halide such as thionyl halide are heated in the aforesaid aprotic solvent to form an acid halide, and subsequently, the acid halide is reacted with α-tocopherol in the aforesaid aprotic solvent in the presence of a tertiary amine such as pyridine and triethylamine. The suitable mole ratio of the 5-substituted picolinic acid chloride to α-tocopherol is 1:0.5–2.0, and the reaction temperature is from −20° C. to room temperature.

The desired final compound may be isolated from the reaction mixture and purified by usual methods, such as solvent extraction, column chromatography or recrystallization. Generally, products insoluble in the reaction mixture, if any, are removed by filtration, and the filtrate is washed with a dilute acid and a dilute aqueous solution of an alkali bicarbonate. Subsequent removal of the solvent gives the desired compound. If required, it can be further purified by column chromatography or recrystallization.

The starting compound of formula (II) can be produced in a manner known per se. For example, it is produced by oxidizing a 5-substituted-α-picoline with selenium dioxide. Advantageously, this oxidation is carried out in pyridine. The reaction is completed by heating 1 mole of the 5-substituted-α-picoline and 1.5 to 4.0 moles of selenium dioxide under reflux for 5 to 24 hours. Metallic selenium is separated from the reaction mixture, and pyridine is distilled off from the pyridine solution. The residue is dissolved in water and neutralized with an acid, whereby the desired 5-substituted picolinic acid is isolated.

Those compounds of formula (II) is which Q is a sulfur atom are novel compounds not described in the prior literature, and can be produced, for example, by reacting 5-mercaptopicolinic acid with a compound of formula RX in which R is as defined and X represents a halogen such as chloro, bromo or iodo or an easily eliminable group such as mesyl or tosyl. The reaction is carried out in a solvent such as acetone, methanol, or ethanol in the presence of an excess of an alkali carbonate, and 1 mole of 5-mercaptopicolinic acid is reacted with 1 to 2.0 moles of the compound RX. The reaction usually proceeds at room temperature. The desired 5-substituted picolinic acid is isolated from the reaction mixture and purified usually by extraction or recrystallization.

Referential Examples given hereinbelow show the production of compounds of formula (III) in which Q is S, and their melting points, their dopamine β-hydroxylase inhibiting activities.

The 5-substituted picolinic acid esters of formula (I) produced as above show hypotensive activity comparable to the 5-substituted picolic acids, and this activity generally lasts longer. In addition, the undesirable toxicity and side-effects of the 5-substituted picolinic acid can be markedly reduced.

Thus, according to this invention, there is provided a pharmaceutical composition for the treatment of hypertension, composed of a hypotensively effective amount of an α-tocopheryl 5-substituted picolinate of the formula

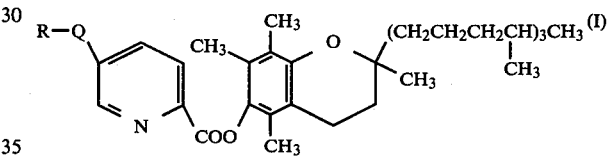
(I)

wherein R represents an alkyl group which may have a substituent, a lower alkenyl group, a phenyl(lower alkyl) group, or a phenyl group which may have a substituent, and Q represents a methylene group or an oxygen or sulfur atom, or its pharmaceutically acceptable acid addition salt, and a pharmaceutically acceptable diluent or carrier.

The pharmaceutically acceptable acid addition salt can be produced by contacting the compound of formula (I) with a pharmaceutically acceptable acid in a manner known per se. The salt-forming reaction is carried out, for example, by dissolving the compound of formula (I) in an aprotic solvent such as hexane and adding one equivalent of an acid to the solution. The resulting pharmaceutically acceptable acid addition salt is separated as a solid.

Such acid addition salts may, for example, be pharmaceutically acceptable addition salts of the 5-substituted picolinates with inorganic or organic acids such as hydrochloric acid, nitric acid, sulfuric acid, phosphoric acid, methanesulfonic acid, toluenesulfonic acid, acetic acid, propionic acid, tartaric acid, maleic acid, fumaric acid and malic acid.

Known liquid or solid diluents or carriers for various drug forms can be used as the pharmaceutically acceptable diluent or carrier for the pharmaceutical composition of this invention. Examples include solid diluents or carriers such as lactose, corn starch, crystalline cellulose, carboxymethylcellulose, hydroxypropyl cellulose, gum arabic, carnauba wax, beeswax and magnesium stearate; and liquid diluents or carriers such as sesame oil, olive oil, cottonseed oil, soybean oil, peanut oil, purified rice bran oil and propylene glycol.

The pharmaceutical composition of this invention may be in various forms such as soft capsules, hard capsules, granules and tablets. The amount of the compound of formula (I) included in the pharmaceutical composition of this invention in such forms may be properly varied. For example, it may be about 20 to about 100% based on the weight of the composition.

Usually, the pharmaceutical composition of this invention is administered orally, and its dose is about 50 mg to about 1.5 g/body, for example.

By taking up α-tocopheryl 5-butylpicolinate as a preferred example of the compound of formula (I) of this invention, pharmacological tests were carried out as follows:

(1) Hypotensive action dl-α-tocopheryl 5-butylpicolinate and dl-α-tocopherol were used after they were each dissolved in a suitable amount of ethyl ether, mixed with a solution containing 2% of Tween 80 and 2% of Span 40 and after removing ethyl ether, uniformly emulsified. 5-Butylpicolinic acid was used as a solution in 2% Tween 80+2% Span.

Spontaneous hypertensive rats (male, body weight 350 to 370 g) and Wistar rats with a normal blood pressure level (female, body weight 250 to 270 g), three per group, were used. Without anesthesia, the pressure of the tail artery was measured by plethysmography. The results are shown in Tables 1 and 2.

TABLE 1

(Spontaneous hypertensive rats, orally administered)

| Compound | Dose (mg/kg) | Blood pressure lowering rate (%) | | | |
|---|---|---|---|---|---|
| | | 1h | 2h | 3h | 4h |
| A | 37.5 (11.36) | 29.0 | 18.3 | 13.0 | 0 |
| " | 9.375 (2.841) | 20.3 | 3.2 | 0 | 0 |
| B | 12.5 (12.5) | 35.7 | 21.7 | 11.8 | 0 |
| " | 3.125 (3.125) | 16.9 | 0.7 | 0 | 0 |
| C | 37.5 (12.5) | 40.9 | 28.2 | 16.4 | 0 |
| " | 9.375 (3.125) | 16.0 | 5.5 | 0 | 0 |

TABLE 2

(Normotensive Wistar rats, orally administered)

| Compound | Dose (mg/kg) | Blood pressure lowering rate (%) | | | |
|---|---|---|---|---|---|
| | | 1h | 2h | 3h | 4h |
| A | 150 (45.45) | 2.4 | 18.3 | 8.7 | 0 |
| B | 50 (50) | 27.0 | 33.5 | 26.2 | 0 |

In Tables 1 and 2, compound A denotes dl-α-tocopheryl 5-butylpicolinate; compound B, 5-butylpicolinic acid; compound C, a mixture of 5-butylpicolinic acid and dl-α-tocopherol (weight ratio 2:1, nearly equimolar); and the parenthesized figures in the column of "Dose" are values calculated for 5-butylpicolinic acid.

It is seen from the results shown in Tables 1 and 2 that the dl-α-tocopheryl 5-butylpicolinate has a strong hypotensive action on spontaneous hypertensive rats substantially equivalent to 5-butylpicolinic acid or a mixture of it with dl-α-tocopherol as a control. On the other hand, the blood pressure lowering effect of dl-α-tocopheryl 5-butylpicolinate or normotensive rats (with normal levels of blood pressure) was weaker both in strength and duration than that of 5-butylpicolinic acid. From this, it can be concluded that dl-α-cocopheryl 5-butylpicolinate has a hypotensive action which is more selective for hypertension than 5-butylpicolinic acid.

(2) Acute toxicity test ddY-Strain female mice (body weight about 20 g), five per group, were used and each of the test compounds was orally or intraperitoneally administered, and two days after the administration, the number of dead mice was counted. From it, the acute toxicity $LD_{50}$ of each of the compounds was determined by the Behrens-Kräerber method. The results are shown in Table 3.

TABLE 3

| | (acute toxicity $LD_{50}$, mg/kg) | | | |
|---|---|---|---|---|
| Compound | Orally administered | | Intraperitoneally administered | |
| A | >4000 | (>1212) | >4000 | (>1212) |
| B | 180 | (180) | 89 | (89) |
| C | 630 | (210) | 293 | (98) |

In Table 3, the compounds A, B and C and the parenthesized figures are the same as in Tables 1 and 2.

It is seen from the results shown in Table 3 that no case of death was noted in groups to which dl-α-tocopheryl 5-butylpicolinate was administered orally and intraperitoneally, respectively, even at the highest dose of 4000 mg/kg (1212 mg/kg calculated for 5-butylpicolinic acid). On the other hand, the $LD_{50}$ of the 5-butylpicolinic acid alone or the $LD_{50}$ of a mixture of 5-butylpicolinic acid and dl-α-tocopherol were 180 and 210 mg/kg (oral) and 89 and 98 mg/kg (intraperitoneal) both calculated for 5-butylpicolinic acid. In other words, the toxicity of 5-butylpicolinic acid was not reduced by the simple addition of dl-α-tocopherol, but was markedly decreased when it was esterified with dl-α-tocopherol.

(3) Side-effects dl-α-Tocopheryl 5-butylpicolinate of the invention and 5-butylpicolinic acid as a control were administered orally to rats for 4 consecutive days at a dose of 300 mg/kg (90.9 mg/kg calculated for 5-butylpicolinic acid) and 100 mg/kg. Then, the stomach of each rat was incised and observed for the occurrence of a gastric trouble. Light degrees of edema, congestion, or bleeding were noted in the stomachs of all cases (five rats) in a control group, but no change was observed in the stomachs of a group of rats to which dl-α-tocopheryl 5-butylpicolinate was administered.

The following Tables 4 and 5 summarize the maximum blood pressure lowering rates and the acute toxicity values ($LD_{50}$ values) of other typical examples of the compound of formula (I).

TABLE 4

| | | Maximum blood pressure lowering rates (%) | |
|---|---|---|---|
| R in formula (I) | Q in formula (I) | Maximum blood pressure lowering rate (%) of the compound of the invention | Maximum blood pressure lowering rate (%) of the 5-substituted picolinic acid |
| $BrCH_2CHBrCH_2$ | $CH_2$ | 53 | 50 |
| $ClCH_2CHClCH_2$ | $CH_2$ | 53 | 53 |
| $BrCH_2(CH_2)_2$ | $CH_2$ | 48 | 49 |
| $ClCH_2(CH_2)_2$ | $CH_2$ | 50 | 46 |

TABLE 4-continued

Maximum blood pressure lowering rates (%)

| R in formula (I) | Q in formula (I) | Maximum blood pressure lowering rate (%) of the compound of the invention | Maximum blood pressure lowering rate (%) of the 5-substituted picolinic acid |
|---|---|---|---|
|  | $CH_2$ | 41 | 39 |
| $CH_3(CH_2)_3$ | O | 36 | 31 |
| $ClCH_2(CH_2)_3$ | O | 40 | 43 |
| 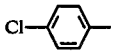 | O | 48 | 56 |
| $CH_3(CH_2)_3$ | S | 39 | 36 |
| $CH_3(CH_2)_2$ | S | 31 | 33 |
| $ClCH_2(CH_2)_2$ | S | 43 | 48 |

In Table 4, 0.01 mmol/kg of each compound was orally administered to spontareous hypertensive rats.

TABLE 5

| | | Acute toxicity $LD_{50}$ (mg/kg) | |
|---|---|---|---|
| R in formula (I) | Q in formula (I) | $LD_{50}$ of the compound of the invention | $LD_{50}$ of the 5-substituted picolinic acid |
| $BrCH_2CHBrCH_2$ | $CH_2$ | >4000 | 110 |
| $ClCH_2CHClCH_2$ | $CH_2$ | >4000 | 41 |
| $BrCH_2(CH_2)_2$ | $CH_2$ | >4000 | 46 |
| $ClCH_2(CH_2)_2$ | $CH_2$ | >4000 | 44 |
|  | $CH_2$ | >4000 | 135 |
| $CH_3(CH_2)_3$ | O | >4000 | 134 |
| $ClCH_2(CH_2)_3$ | O | >4000 | 172 |
| 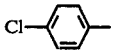 | O | >4000 | 123 |
| $CH_3(CH_2)_3$ | S | >4000 | 143 |
| $CH_2(CH_2)_2$ | S | >4000 | 167 |
| $ClCH_2(CH_2)_2$ | S | >4000 | 179 |

In Table 5, each compound was intraperitoneally administered to mice.

The following Referential Examples and Examples illustrate the present invention more specifically.

REFERENTIAL EXAMPLE 1

1.2 g of 5-mercaptopicolinic acid was dissolved in 100 ml of a 5% aqueous solution of sodium carbonate, and 100 ml of acetone, 4.4 g of anhydrous sodium carbonate and 3.0 g of n-butyl bromide were added. The mixture was stirred at room temperature for 3 hours. After the reaction, acetone was distilled off under reduced pressure from the reaction mixture. Hydrochloric acid was added to the residue to neutralize it to a pH of 2.0, and then it was extracted with ethyl acetate. Recrystallization of the extract from hydrous ethanol gave 0.85 g of 5-n-butylthiopicolinic acid having a melting point of 99° C.

The 50% dopamine β-hydroxylase inhibitory concentration of this product was $5.1 \times 10^{-7}$ M.

REFERENTIAL EXAMPLE 2

The compounds shown in Table 6 were produced in the same way as in Referential Example 1. The melting points of these compounds, the recrystallizing solvents used, and the 50% dopamine β-hydroxylase inhibitory concentrations of these compounds are shown in Table 6.

TABLE 6

$$\text{R-S}\diagup\diagdown\diagup\text{CH=CH}\diagdown\text{C(COOH)=N}$$

| R in formula (I) | Melting point (°C.) | Recrystallizing solvent | 50% dopamine β-hydroxylase inhibitory concentration (moles/liter) |
|---|---|---|---|
| n-Propyl | 103 | Benzene-hexane | $7.0 \times 10^{-7}$ |
| n-Octyl | 93-96 | Hydrous ethanol | $2.3 \times 10^{-5}$ |
| i-Pentyl | 103 (decomp.) | Hydrous acetone | $2.1 \times 10^{-7}$ |
| Methyl | 145 | Hydrous ethanol | $7.5 \times 10^{-6}$ |
| 3-Chloropropyl | 102 | Hydrous acetone | $5.5 \times 10^{-7}$ |
| Benzyl | 172-175 | Hydrous ethanol | $2.8 \times 10^{-7}$ |
| Allyl | 108-109 | Water | $5.5 \times 10^{-7}$ |

EXAMPLE 1

3.6 g of 5-butylpicolinic acid and 4.3 g of dl-α-tocopherol were dissolved in 40 ml of methylene chloride, and subsequently, a solution of 4.2 g of dicyclohexylcarbodiimide in 20 ml of methylene chloride was added. The mixture was stirred at room temperature for 24 hours. The insoluble matter was removed by filtration, and then methylene chloride was distilled off. The residue was dissolved in hexane, and the insoluble matter was removed by filtration. The residue was chromatographed on a column of silica gel using benzene/ethyl acetate (4:1) as an eluent to give 5.5 g of dl-α-tocopheryl 5-butylpipcoinate as a slighty yellow oil.

Elemental analysis for $C_{37}H_{61}NO_3$:

| | C | H | N |
|---|---|---|---|
| Calculated (%) | 79.14 | 10.39 | 2.37 |
| Found (%) | 78.89 | 10.71 | 2.10 |

IR $\nu_{max}^{neat}$(cm$^{-1}$): 2920, 2855, 1755, 1725, 1570, 1460, 1300, 1240, 1100, 755.

UV $\lambda_{max}^{EtOH}$(nm): 227 (ε=21,700), 280 (ε=8,000).

NMR (CCl$_4$, 60 Mz) δppm: 0.7-3.0 (m, 58H), 7.5 (q, 1H), 8.0(d, 1H), 8.5(d, 1H).

EXAMPLE 2

Ten milliliters of benzene was added to 4.51 g of 5-butylpicolinic acid, and 9 g of thionyl chloride was further added. The mixture was heated under reflux for 22 minutes. The excess of thionyl chloride and benzene were disiled off under reduced pressure, and 10 ml of benzene was added to the residue. The mixture was cooled to 0° C. and stirred. To the solution was added dropwise a solution of 5 g of dl-α-tocopherol in 4.25 ml of pyridine to perform the reaction for 1 hour and 40 minutes. The insoluble matter was removed by filtration from the reaction mixture, and the residue was washed with water, 1 N hydrochloric acid, water, a saturated aqueous solution of sodium bicarbonate and a saturated aqueous solution of sodium chloride in this order. Benzene was distilled off, and the residue was chromatographed on a silica gel column using benzene/ethyl acetate (4:1) as an eluent to give 3.2 g of dl-α-tocopheryl 5-butylpicolinate.

EXAMPLE 3

The same procedure as in Example 1 was repeated except that 3.8 g of 5-pentylpicolinic acid was used instead of the 5-butylpicolinic acid. There was obtained 5.6 g of dl-α-tocopheryl 5-pentylpicolinate as a slightly yellow oil.

Elemental analysis for $C_{40}H_{63}NO_3$:

|  | C | H | N |
| --- | --- | --- | --- |
| Calculated (%) | 79.29 | 10.48 | 2.31 |
| Found (%) | 79.16 | 10.85 | 1.96 |

IR $\nu_{max}^{neat}(cm^{-1})$: 2920, 2850, 1750, 1725, 1570, 1460, 1300, 1240, 1100, 755.

UV $\lambda_{max}^{EtOH}(nm)$: 227 ($\epsilon$=24,400), 280 ($\epsilon$=8,970).

NMR (CCl$_4$, 60 Mz) δppm: 0.6–3.0(m, 60H, 7.5(q, 1H), 8.0(d, 1H), 8.5(d, 1H).

EXAMPLE 4

2.42 g of 5-(3,4-dibromobutyl)picolinic acid, 2.15 g of dl-α-tocopherol and 4.0 ml of triethylamine were dissolved in 15 ml of methylene chloride, and with stirring under ice cooling, a solution of 1.0 ml of phosphorus oxychloride in 5 ml of methylene chloride was added dropwise. The reaction was performed at this temperature for 3 hours. The reaction mixture was washed with 2 N hydrochloric acid, and then with water, and dried. Then, methylene chloride was distilled off. The residue was chromatographed on a column of silica gel using benzene/ethyl acetate (4:1) as an eluent to give 3.03 g of dl-α-tocopheryl 5-(3,4-dibromobutyl)picolinate as a slightly yellow oil.

IR $\nu_{max}^{neat}(cm^{-1})$: 2920, 2850, 1745, 1722, 1570, 1460, 1380, 1300, 1240, 1100, 704.

NMR (CDCl$_3$, 60 Mz) δppm: 0.6–2.8(m, 53H), 3.65(d, 2H), 3.85–4.35(m, 1H), 7.72(q, 1H), 8.25(d, 1H), 8.75(d, 1H).

EXAMPLES 5 TO 9

In the same way as in Example 4, the following compounds were produced from dl-α-tocopherol and the corresponding 5-substituted picolinic acids.

dl-α-tocopheryl 5-(3,4-dichlorobutyl)picolinate (Example 5)

IR $\nu_{max}^{neat}(cm^{-1})$: 2920, 2850, 1745, 1722, 1570, 1470, 1460, 1380, 1300, 1240, 1100, 760.

NMR (CDCl$_3$, 60 Mz) δppm: 0.6–2.8(m, 53H), 3.7(d, 2H), 3.85–4.2(m, 1H), 7.75(q, 1H), 8.25(d, 1H), 8.75(d, 1H).

dl-α-tocopheryl 5-(4-bromobutyl)picolinate (Example 6)

IR $\nu_{max}^{neat}(cm^{-1})$: 2920, 2820, 1750, 1720, 1465, 1460, 1375, 1300, 1240, 1100.

NMR (CDCl$_3$, 60 Mz) δppm: 0.6–2.9(m, 55H), 3.4(t, 2H), 7.75(q, 1H), 8.2(d, 1H), 8.65(d, 1H).

dl-α-tocopheryl 5-(4-chlorobutyl)picolinate (Example 7)

IR $\nu_{max}^{neat}(cm^{-1})$: 2920, 2850, 1750, 1730, 1465, 1460, 1375, 1300, 1240, 1100.

NMR (CDCl$_3$, 60 Mz) δppm: 0.6–2.9(m, 55H), 3.5(t, 2H), 7.75(q, 1H), 8.2(d, 1H), 8.65(d, 1H).

dl-α-tocopheryl 5-(4-acetoxybutyl)picolinate (Example 8)

IR $\nu_{max}^{neat}(cm^{-1})$: 2920, 2850, 1750, 1730, 1722, 1465, 1460, 1380, 1300, 1250, 1100, 1040.

NMR (CDCl$_3$, 60 Mz) δppm: 0.6–3.0(m, 55H), 2.05(s, 3H), 4.1(t, 2H), 7.7(q, 1H), 8.25(d, 1H), 8.7(d, 1H).

dl-α-tocopheryl 5-benzylpicolinate (Example 9)

IR $\nu_{max}^{neat}(cm^{-1})$: 2920, 2850, 1750, 1725, 1600, 1570, 1460, 1310, 1240, 1100, 755.

NMR (CDCl$_3$, 60 Mz) δppm: 0.6–2.8(m, 49H), 4.2(s, 2H), 7.3(s, 5H), 7.6(q, 1H), 8.2(d, 1H), 8.6(d, 1H).

EXAMPLE 10

3.92 g of 5-(4-hydroxybutyl)picolinic acid was dissolved in 20 ml of pyridine, and with stirring under ice cooling, a solution of 4.6 g of carbobenzyloxy chloride in 20 ml of toluene was added dropwise. Under ice cooling, the mixture was reacted for 2 hours. Then, the reaction mixture was poured into ice water, and extracted with toluene. The extract was washed successively with water, 1 N hydrochloric acid and then with water, and the toluene was distilled off to give 5.7 g of 5-(4-carbobenzyloxybutyl)picolinic acid.

5.7 g of 5-(4-carbobenzyloxybutyl)picolinic acid and 7.7 g of dl-α-tocopherol were dissolved in 50 ml of methylene chloride, and 7.5 g of dicyclohexylcarbodiimide was added. The reaction was performed overnight at room temperature. The dicyclohexylurea precipitated was removed by filtration, and methylene chloride was distilled off from the filtrate.

The residue was dissolved in 100 ml of ethanol, and 1.5 g of 5% palladium on carbon was added. It was hydrogenated at room temperature for 3 hours in a stream of hydrogen. The catalyst was removed by filtration from the reaction mixture, and ethanol was distilled off. The residue was chromatographed on a column of silica gel using benzene/ethyl acetate (4:1) as an eluent to give 2.13 g of dl-α-tocopheryl 5-(4-hydroxybutyl)picolinate as a lightly yellow oil.

IR $\nu_{max}^{neat}(cm^{-1})$: 3450, 2920, 2850, 1745, 1730, 1720, 1460, 1375, 1300, 1250, 1100, 1040.

NMR (CDCl$_3$, 60 Mz) δppm: 0–3.0 (m, 55H), 2.9(t, 1H), 3.8–4.2(m, 2H), 7.7(q, 1H), 8.25(d, 1H), 8.7(d, 1H).

EXAMPLE 11

10 ml of toluene was added to 3.8 g of 5-ethylpicolinic acid, and 9 g of thionyl chloride was added. The mixture was heated at 80° C. for 20 minutes. The solvent was distilled off under reduced pressure. The residue was dissolved in 10 ml of toluene and the solution was cooled to 0° C. With stirring, a solution of 5 g of dl-α-tocopeherol in 4.25 ml of pyridine was added dropwise for 1.5 hours. The insoluble matter was filtered off from the reaction mixture, and the residue was washed successively with water, 1 N hydrochloric acid, water, and a saturated aqueous solution of sodium bicarbonate in this order. The toluene was distilled off, and the residue was chromatographed on a column of silica gel using benzene/ethyl acetate (4:1) as an eluent to give 1.3 g of dl-α-tocopheryl 5-ethylpicolinate as a slightly yellow oil.

IR $\nu_{max}^{neat}$(cm$^{-1}$): 2920, 2855, 1750, 1725, 1570, 1460, 1300, 1240, 1100, 755.

NMR (CCl$_4$, 60 Mz) δppm: 0.7–3.0(m, 54H), 7.5(q, 1H), 8.0(d, 1H), 8.5(d, 1H).

EXAMPLES 12 AND 13

In the same way as in Example 1, the following compounds were produced from dl-α-tocopherol and the corresponding 5-substituted picolinic acids.

dl-α-tocopheryl 5-n-hexylpicolinate (Example 12)

IR $\nu_{max}^{neat}$(cm$^{-1}$): 2920, 2850, 1755, 1725, 1570, 1460, 1300, 1240, 1100, 755.

NMR (CCl$_4$, 60 Mz) δppm: 0.7–3.0 (m, 62H), 7.5(q, 1H), 8.0(d, 1H), 8.5(d, 1H).

dl-α-tocopheryl 5-(3-buten-1-yl)picolinate (Example 13)

IR $\nu_{max}^{neat}$(cm$^{-1}$): 2920, 2850, 1750, 1722, 1465, 1460, 1375, 1300, 1250, 1100, 1010, 905.

NMR (CDCl$_3$, 60 Mz) δppm: 0.6–2.9(m, 53H), 5.1(t, 2H), 5.5–5.9(m, 1H), 7.7(q, 1H), 8.2 (d, 1H), 8.5(d, 1H).

EXAMPLES 14 TO 17

In the same way as in Example 1, the following compounds were produced from dl-α-tocopherol and the corresponding 5-substituted picolinic acids.

dl-α-tocopheryl 5-butyloxypicolinate (Example 14)

Melting point: 46°–48° C.

IR $\nu_{max}^{neat}$(cm$^{-1}$): 2920, 2850, 1755, 1725, 1580, 1475, 1465, 1380, 1320, 1255, 1100.

NMR (CDCl$_3$, 60 Mz) δppm: 0.6–2.8(m, 56H), 4.1(t, 2H), 7.3(q, 1H), 8.1(d, 1H), 8.5(d, 1H).

dl-α-tocopheryl 5-propyloxypicolinate (Example 15)

Melting point: 55°–57° C.

IR $\nu_{max}^{neat}$(cm$^{-1}$): 2920, 2850, 1750, 1720, 1575, 1470, 1460, 1380, 1320, 1230, 1100.

NMR (CDCl$_3$, 60 Mz) δppm: 0.6–2.8(m, 54H), 4.05(t, 2H), 7.3(q, 1H), 8.25(d, 1H), 8.5(d, 1H).

dl-α-tocopheryl 5-(4-chlorobutyloxy)picolinate (Example 16)

IR $\nu_{max}^{neat}$(cm$^{-1}$): 2920, 2850, 1740, 1720, 1575, 1470, 1460, 1380, 1320, 1235, 1100, 1080.

NMR (CDCl$_3$, 60 Mz) δppm: 0.6–2.8(m, 53H), 3.7(t, 2H), 4.1(t, 2H), 7.7(q, 1H), 8.2 (d, 1H), 8.7(d, 1H).

dl-α-tocopheryl 5-(4-chlorophenyloxy)picolinate (Example 17)

IR $\nu_{max}^{neat}$(cm$^{-1}$): 2920, 2850, 1740, 1720, 1605, 1570, 1460, 1380, 1320, 1235, 1100.

NMR (CDCl$_3$, 60 Mz) δppm: 0.6–2.8(m, 49H), 6.8(q, 2H), 7.2(q, 2H), 7.8(q, 1H), 8.2(d, 1H), 8.7(d, 1H).

EXAMPLES 18 TO 24

In the same way as in Example 1, the following compounds were produced from dl-α-tocopherol and the corresponding 5-substituted picolinic acids.

dl-α-tocopheryl 5-butylthiopicolinate (Example 18)

IR $\nu_{max}^{neat}$(cm$^{-1}$): 2920, 2850, 1750, 1720, 1570, 1460, 1380, 1300, 1235, 1100.

NMR (CDCl$_3$, 60 Mz) δppm: 0.6–2.8(m, 56H), 3.0(t, 2H), 7.7(q, 1H), 8.15(d, 1H), 8.7(d, 1H).

dl-α-tocopheryl 5-n-octylthiopicolate (Example 19)

IR $\nu_{max}^{neat}$(cm$^{-1}$): 2920, 2850, 1750, 1722, 1565, 1470, 1460, 1380, 1310, 1230, 1100, 1070, 780.

NMR (CDCl$_3$, 60 Mz) δppm: 0.6–2.8(m, 64H), 3.0(t, 2H), 7.65(q, 1H), 8.1(d, 1H), 8.65(d, 1H).

dl-α-tocopheryl 5-isopentylthiopicolate (Example 20)

IR $\nu_{max}^{neat}$(cm$^{-1}$): 2920, 2850, 1750, 1725, 1565, 1470, 1460, 1380, 1305, 1240, 1100, 1020.

dl-α-tocopheryl 5-methylthiopicolate (Example 21)

IR $\nu_{max}^{neat}$(cm$^{-1}$): 2920, 2820, 1750, 1722, 1465, 1380, 1305, 1105, 1080.

NMR (CDCl$_3$, 60 Mz) δppm: 0.6–2.8(m, 49H), 2.55 (s, 3H), 7.75(q, 1H), 8.23(d, 1H), 8.73(d, 1H).

dl-α-tocopheryl 5-benzylthiopicolate (Example 22)

IR $\nu_{max}^{neat}$(cm$^{-1}$): 2920, 2820, 1750, 1720, 1465, 1460, 1375, 1300, 1240, 1100.

NMR (CDCl$_3$, 60 Mz) δppm: 0.6–2.9(m, 55H), 3.4(t, 2H), 7.75(q, 1H), 8.2(d, 1H), 8.65(d, 1H).

dl-α-tocopheryl 5-(3-chloropropylthio)picolinate (Example 23)

IR $\nu_{max}^{neat}$(cm$^{-1}$): 2920, 2820, 1740, 1722, 1465, 1460, 1375, 1320, 1235, 1100, 1080.

NMR (CDCl$_3$, 60 Mz) δppm: 0.6–2.8(m, 51H), 3.25(t, 2H), 3.7(t, 2H), 7.75(q, 1H), 8.25(d, 1H), 8.25(d, 1H).

dl-α-tocopheryl 5-allylthiopicolate (Example 24)

IR $\nu_{max}^{neat}$(cm$^{-1}$): 2920, 2850, 1740, 1722, 1465, 1460, 1375, 1300, 1235, 1100, 1010.

NMR (CDCl$_3$, 60 Mz) δppm: 0.6–2.8(m, 49H), 4.2(d, 2H), 5.0–5.5(m, 2H), 5.75–6.25(m, 1H), 7.7(q, 1H), 8.2(d, 1H), 8.5(d, 1H).

EXAMPLE 25

1.97 g of propylthiopicolinic acid and 2.15 g of dl-α-tocopherol were dissolved in 25 ml of methylene chloride and 2.06 g of dicyclohexylcarbodiimide was added. The mixture was stirred overnight to perform the reaction. The insoluble dicyclohexylurea was removed by filtration from the reaction mixture, and methylene chloride was distilled off. The residue was chromatographed on a column of silica gel using benzene/ethyl acetate (4:1) as an eluent to give 2.05 g of dl-α-tocopheryl 5-propylthiopicolate as a slightly yellow oil.

IR $\nu_{max}^{neat}$(cm$^{-1}$): 2920, 2850, 1745, 1720, 1560, 1460, 1375, 1300, 1230, 1100.

NMR (CDCl$_3$, 60 Mz) δppm: 0.6–2.8(m, 54H), 3.0(t, 2H), 7.7(q, 1H), 8.2(d, 1H), 8.7(d, 1H).

What we claim is:

1. An α-tocopheryl 5-substituted picolinate of the formula

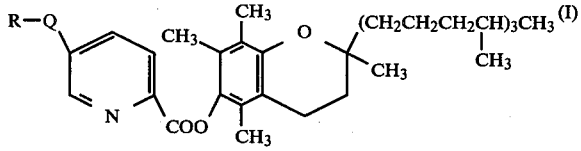

wherein R represents a linear or branched C$_1$–C$_8$ alkyl group which may be mono- or di-substituted by a substituent or substituents selected from the class consisting of halogen atoms, acetoxy groups, hydroxyl groups and $C_1$–$C_4$ alkyl ether groups, a $C_2$–$C_5$ alkenyl group, a phenyl ($C_1$–$C_2$) alkyl group, or a phenyl group which may be mono- or di-substituted by a substituent or substituents selected from the class consisting of halogen atoms and nitro groups, and Q represents a methylene group or an oxygen or sulfur atom, or a pharmaceutically acceptable acid addition salt thereof.

2. The comound of claim 1 wherein the α-tocopheryl 5-substituted picolinate is dl-α-tocopheryl 5-butylpicolinate.

3. The compound of claim 1 wherein the α-tocopheryl 5-substituted picolinate is dl-α-tocopheryl 5-pentylpicolinate.

4. The compound of claim 1 wherein the α-tocopheryl 5-substituted picolinate is dl-α-tocopheryl 5-(3,4-dibromobutyl)picolinate.

5. The compound of claim 1 wherein the α-tocopheryl 5-substituted picolinate is dl-α-tocopheryl 5-(3,4-dichlorobutyl)picolinate.

6. The compound of claim 1 wherein the α-tocopheryl 5-substituted picolinate is dl-α-tocopheryl 5-(4-bromobutyl)picolinate.

7. The compound of claim 1 wherein the α-tocopheryl 5-substituted picolinate is dl-α-tocopheryl 5-(4-chlorobutyl)picolinate.

8. The compound of claim 1 wherein the α-tocopheryl 5-substituted picolinate is dl-α-tocopheryl 5-(4-acetoxybutyl)picolinate.

9. The compound of claim 1 where the α-tocopheryl 5-substituted picolinate is dl-α-tocopheryl 5-benzylpicolinate.

10. The compound of claim 1 wherein the α-tocopheryl 5-substituted picolinate is dl-α-tocopheryl 5-(4-hydroxybutyl)picolinate.

11. The compound of claim 1 wherein the α-tocopheryl 5-substituted picolinate is dl-α-tocopheryl 5-ethylpicolinate.

12. The compound of claim 1 wherein the α-tocopheryl 5-substituted picolinate is dl-α-tocopheryl 5-n-hexylpicolinate.

13. The compound of claim 1 wherein the α-tocopheryl 5-substituted picolinate is dl-α-tocopheryl 5-(3-buten-1-yl)picolinate.

14. The compound of claim 1 wherein the α-tocopheryl 5-substituted picolinate is dl-α-tocopheryl 5-butyloxypicolinate.

15. The compound of claim 1 wherein the α-tocopheryl 5-substituted picolinate is dl-α-tocopheryl 5-propyloxypicolinate.

16. The compound of claim 1 wherein the α-tocopheryl 5-substituted picolinate is dl-α-tocopheryl 5-(4-chlorobutyloxy)picolinate.

17. The compound of claim 1 wherein the α-tocopheryl 5-substituted picolinate is dl-α-tocopheryl 5-(4-chlorophenyloxy)picolinate.

18. The compound of claim 1 wherein the α-tocopheryl 5-substituted picolinate is dl-α-tocopheryl 5-butylthiopicolinate.

19. The compound of claim 1 wherein the α-tocopheryl 5-substituted picolinate is dl-α-tocopheryl 5-n-octylthiopicolinate.

20. The compound of claim 1 wherein the α-tocopheryl 5-substituted picolinate is dl-α-tocopheryl 5-isopentylthiopicolinate.

21. The compound of claim 1 wherein the α-tocopheryl 5-substituted picolinate is dl-α-tocopheryl 5-methylthiopicolinate.

22. The compound of claim 1 wherein the α-tocopheryl 5-substituted picolinate is dl-α-tocopheryl 5-benzylthiopicolinate.

23. The compound of claim 1 wherein the α-tocopheryl 5-substituted picolinate is dl-α-tocopheryl 5-(3-chloropropylthio)picolinate.

24. The compound of claim 1 wherein the α-tocopheryl 5-substituted picolinate is dl-α-tocopheryl 5-allylthiopicolinate.

25. The compound of claim 1 wherein the α-tocopheryl 5-substituted picolinate is dl-α-tocopheryl 5-propylthiopicolinate.

26. A pharmaceutical composition for treating hypertension, said composition being composed of a hypotensively effective amount of an α-tocopheryl 5-substituted picolinate of the formula

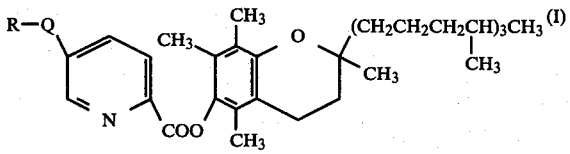

wherein R represents a linear or branched $C_1$–$C_8$ alkyl group which may be mono- or di-substituted by a substituent or substituents selected from the class consisting of halogen atoms, acetoxy groups, hydroxyl groups, and $C_1$–$C_4$ alkyl ether groups, a $C_2$–$C_5$ alkenyl group, a phenyl ($C_1$–$C_2$) alkyl group, or a phenyl group which may be mono- or di-substituted by a substituent or substituents selected from the class consisting of halogen atoms and nitro groups, and Q represents a methylene group or an oxygen or sulfur atom, or a pharmaceutically acceptable acid addition salt, and a pharmaceutically acceptable diluent or carrier.

* * * * *